US005681531A

United States Patent [19]
LaPack et al.

[11] Patent Number: 5,681,531
[45] Date of Patent: Oct. 28, 1997

[54] APPARATUS FOR MIXING AT LEAST PARTIALLY IMMISCIBLE LIQUIDS

[75] Inventors: Mark A. LaPack; James C. Tou; Terry J. Nestrick, all of Midland, Mich.

[73] Assignee: The Dow Chemical Company, Midland, Mich.

[21] Appl. No.: 552,889

[22] Filed: Nov. 3, 1995

Related U.S. Application Data

[62] Division of Ser. No. 337,125, Nov. 10, 1994, Pat. No. 5,482,862, which is a continuation of Ser. No. 680,462, Apr. 4, 1991, abandoned.

[51] Int. Cl.$^6$ .................................................. G01N 35/08
[52] U.S. Cl. .......................... 422/81; 422/68.1; 436/52; 436/54; 436/55; 436/178
[58] Field of Search ...................... 422/62, 68.1, 81; 436/52, 54, 55, 178

[56] References Cited

U.S. PATENT DOCUMENTS

| | | | |
|---|---|---|---|
| 3,190,725 | 6/1965 | Van Den Berg | 422/200 |
| 3,342,727 | 9/1967 | Bringle | 210/15 |
| 3,393,149 | 7/1968 | Conley et al. | 210/42 |
| 3,394,080 | 7/1968 | Hoffman et al. | 210/59 |
| 3,596,767 | 8/1971 | Antonie | 210/96.1 |
| 3,844,170 | 10/1974 | Critten | 73/861.06 |
| 3,847,802 | 11/1974 | Lemke | 210/7 |
| 4,022,575 | 5/1977 | Hansen et al. | 422/81 |
| 4,099,871 | 7/1978 | Sunshara et al. | 356/73 |
| 4,130,481 | 12/1978 | Chase et al. | 210/6 |
| 4,155,978 | 5/1979 | Naono et al. | 422/81 |
| 4,159,248 | 6/1979 | Taylor et al. | 210/96.1 |
| 4,160,734 | 7/1979 | Taylor et al. | 210/96.1 |
| 4,248,085 | 2/1981 | Coulthard | 73/861.06 |
| 4,259,015 | 3/1981 | Wada | 356/336 |
| 4,280,910 | 7/1981 | Baumann | 210/44 |
| 4,341,633 | 7/1982 | Walder | 210/614 |
| 4,383,920 | 5/1983 | Muller et al. | 210/87 |
| 4,396,943 | 8/1983 | Lord et al. | 358/107 |
| 4,437,992 | 3/1984 | Saito et al. | 210/603 |
| 4,486,097 | 12/1984 | Riley | 422/64 |
| 4,504,393 | 3/1985 | Davies | 210/614 |
| 4,510,243 | 4/1985 | Haga et al. | 435/167 |
| 4,516,432 | 5/1985 | Hironaga et al. | 73/861.04 |
| 4,573,761 | 3/1986 | McLachlan et al. | 350/96.24 |
| 4,581,143 | 4/1986 | Pepper, III | 210/614 |
| 4,643,573 | 2/1987 | McLachlan et al. | 356/338 |
| 4,664,513 | 5/1987 | Webb et al. | 356/28 |
| 4,690,755 | 9/1987 | Friedman et al. | 210/96.1 |
| 4,698,158 | 10/1987 | Fujii et al. | 210/610 |
| 4,707,130 | 11/1987 | Hofman | 356/28 |
| 4,729,109 | 3/1988 | Adrian et al. | 364/560 |
| 4,731,185 | 3/1988 | Chen et al. | 210/605 |
| 4,743,753 | 5/1988 | Cheng | 250/227 |
| 4,764,271 | 8/1988 | Acosta | 210/86 |
| 4,783,314 | 11/1988 | Hoots et al. | 422/3 |
| 4,783,750 | 11/1988 | Smith | 364/497 |
| 4,816,158 | 3/1989 | Shimura et al. | 210/610 |
| 4,816,226 | 3/1989 | Jordan et al. | 422/68.1 |
| 4,822,744 | 4/1989 | Bellows | 436/38 |
| 4,853,336 | 8/1989 | Saros et al. | 436/52 |
| 4,855,061 | 8/1989 | Martin | 210/709 |
| 4,898,672 | 2/1990 | Clifft et al. | 210/614 |
| 4,898,829 | 2/1990 | Siepmann et al. | 436/52 |
| 5,233,876 | 8/1993 | LaPack et al. | 73/863.23 |
| 5,270,183 | 12/1993 | Corbett et al. | 435/91.2 |
| 5,482,862 | 1/1996 | LaPack et al. | 436/52 |

FOREIGN PATENT DOCUMENTS 2162636  2/1986  United Kingdom.

*Primary Examiner*—Jill Warden
*Assistant Examiner*—Maureen M. Wallenhorst

[57] ABSTRACT

Apparatus for optimizing a treatment for removing organic substances from a chemical process stream wherein known quantities and kinds of organic or other compounds are injected into and dissolved in the stream prior to treatment thereof. Samples of the compounds are extracted from the stream before and after treatment thereof and compared with one another to determine the efficiency of the treatment. The injecting apparatus is one that enables a substance that is at least partially immiscible with the liquid of the stream to be injected into the stream at a velocity sufficiently great to cause adequate dissolution of the substance in the stream.

6 Claims, 2 Drawing Sheets

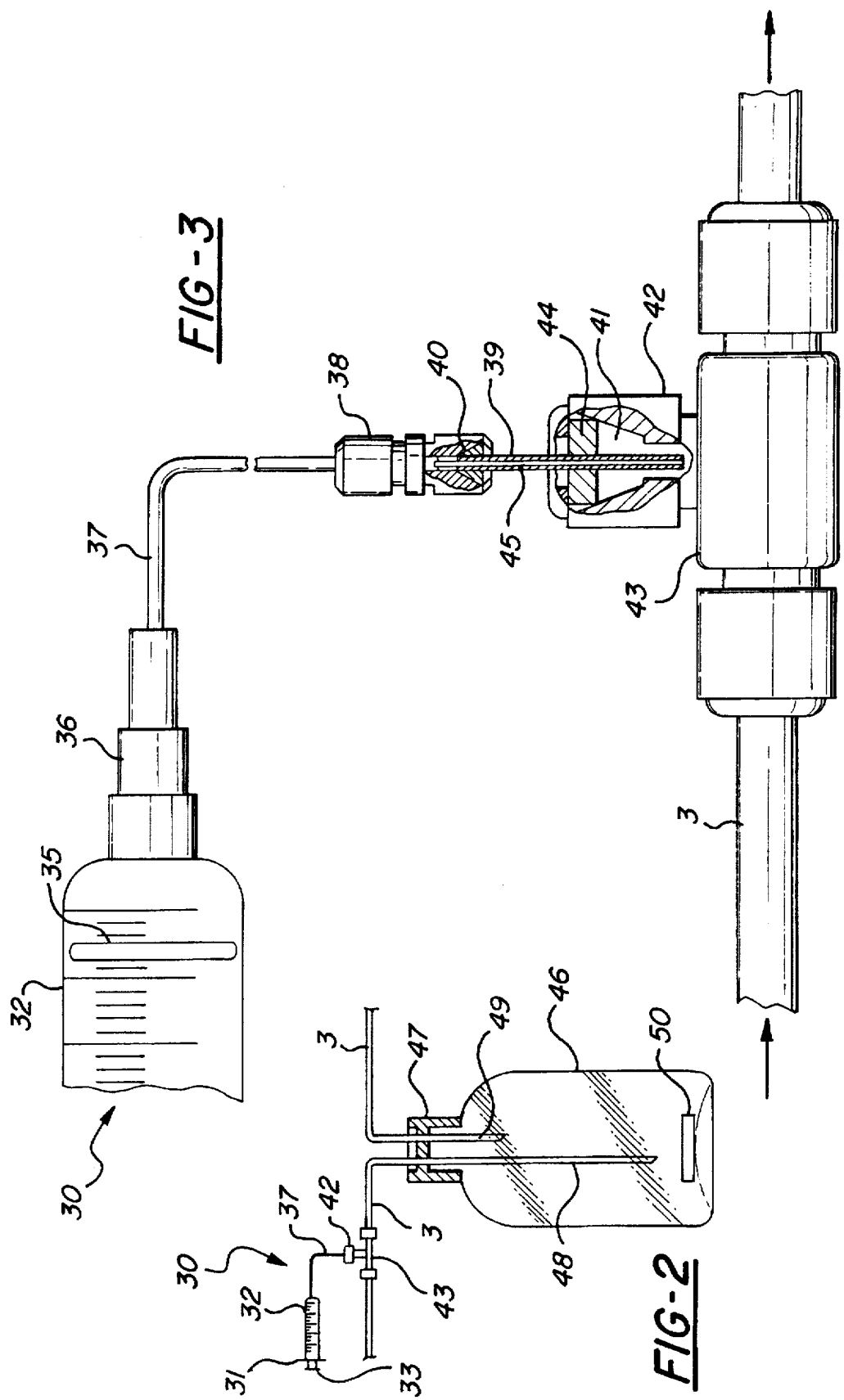

5,681,531

APPARATUS FOR MIXING AT LEAST PARTIALLY IMMISCIBLE LIQUIDS

RELATED APPLICATIONS

This application is a Division of application Ser. No. 08/337,125 filed Nov. 10, 1994, now U. S. Pat. No. 5,482, 862, issued on Jan. 9, 1996 which is a continuation of application Ser. No. 07/680,462 filed Apr. 4, 1991, now abandoned.

This invention relates to apparatus for forming solutions of at least partially immiscible liquids and more particularly to apparatus for dissolving organic or other nominally immiscible compounds in aqueous streams to facilitate the evaluation of the efficiency of processes for extracting such compounds from chemical process streams.

BACKGROUND OF THE INVENTION

In analytical and process technology, it often is desirable to generate a fluid mixture that is composed of components that normally are immiscible with one another. In the case of most analytical techniques, quantitation of a substance in a sample matrix is determined by analyzing the sample and comparing the resultant analytical response with the response obtained from the analysis of prepared standard solutions of the analyte in the same or similar matrix. For example, the quantitative analysis of organic compounds in a wastewater sample is facilitated by analyzing prepared standard solutions of organic compounds in water.

Another application for a solution or mixture of typically immiscible compounds is in a treatment for the destruction of organic chemicals by biodegradation. Typically, the biodegrading mass is supported in and sustained by a water matrix in which many organic compounds may not readily dissolve. Effective treatment of these compounds is highly dependent upon effective mixing of the compounds in the water matrix.

The apparatus according to the invention provides dynamic mixing of otherwise immiscible liquid streams and may be utilized in the processes disclosed in applications Ser. No. 07/680,462, now U.S. Pat. No. 5,233,876 issued Aug. 10, 1993, and Ser. No. 07/680,663, now abandoned.

SUMMARY OF THE INVENTION

Apparatus according to the invention enable organic or other immiscible compounds to be mixed in liquid streams that are to be analyzed or treated in a process.

Apparatus according to the invention is adapted for use in a process wherein the process stream to be analyzed has all or a portion of the influent pumped through a conduit to a treatment zone via a membrane separator or other suitable means for extracting from the influent a sample of a selected analyte of interest. Following treatment of the stream in the treatment zone, the effluent passes through a membrane separator or other suitable means which extracts some or all of the selected analyte remaining in the stream following the treatment. By analyzing the concentrations of the analytes extracted from the influent and effluent streams it is possible to determine the efficiency of the treatment process.

Apparatus and according to the invention enable one or more of the organic or other compounds typically contained in a process stream and immiscible with the liquid constituting the stream to be mixed and treated on-line for subsequent disposal. To determine the most effective treatment to be performed on a process stream containing a specific compound, a known quantity of such compound is injected into a stream and treated, following which the mixture is treated and the treated effluent analyzed to determine how effective the treatment was in removing the compound.

The mixing is accomplished by injecting a known quantity of one or more known immiscible compounds into a liquid stream at such velocity as to ensure dissolution of the compounds in the liquid stream, followed by stirring of the solution and treatment thereof in a treatment zone in such manner as to remove the compounds. The influent stream containing the dissolved compounds may be sampled prior to treatment and the treated effluent stream may be sampled to determine the effectiveness of the treatment to which the influent stream was subjected. Sampling of the influent and effluent streams may be effected by apparatus and methods disclosed in the aforementioned applications.

THE DRAWINGS

Apparatus according to the invention is illustrated in the accompanying drawings, wherein:

FIG. 2 is a diagrammatic view of the injecting or spiking apparatus and associated parts; and FIG. 3 is a greatly enlarged, partly sectional view of a portion of the spiking apparatus.

THE DISCLOSED EMBODIMENT

Figure 1:
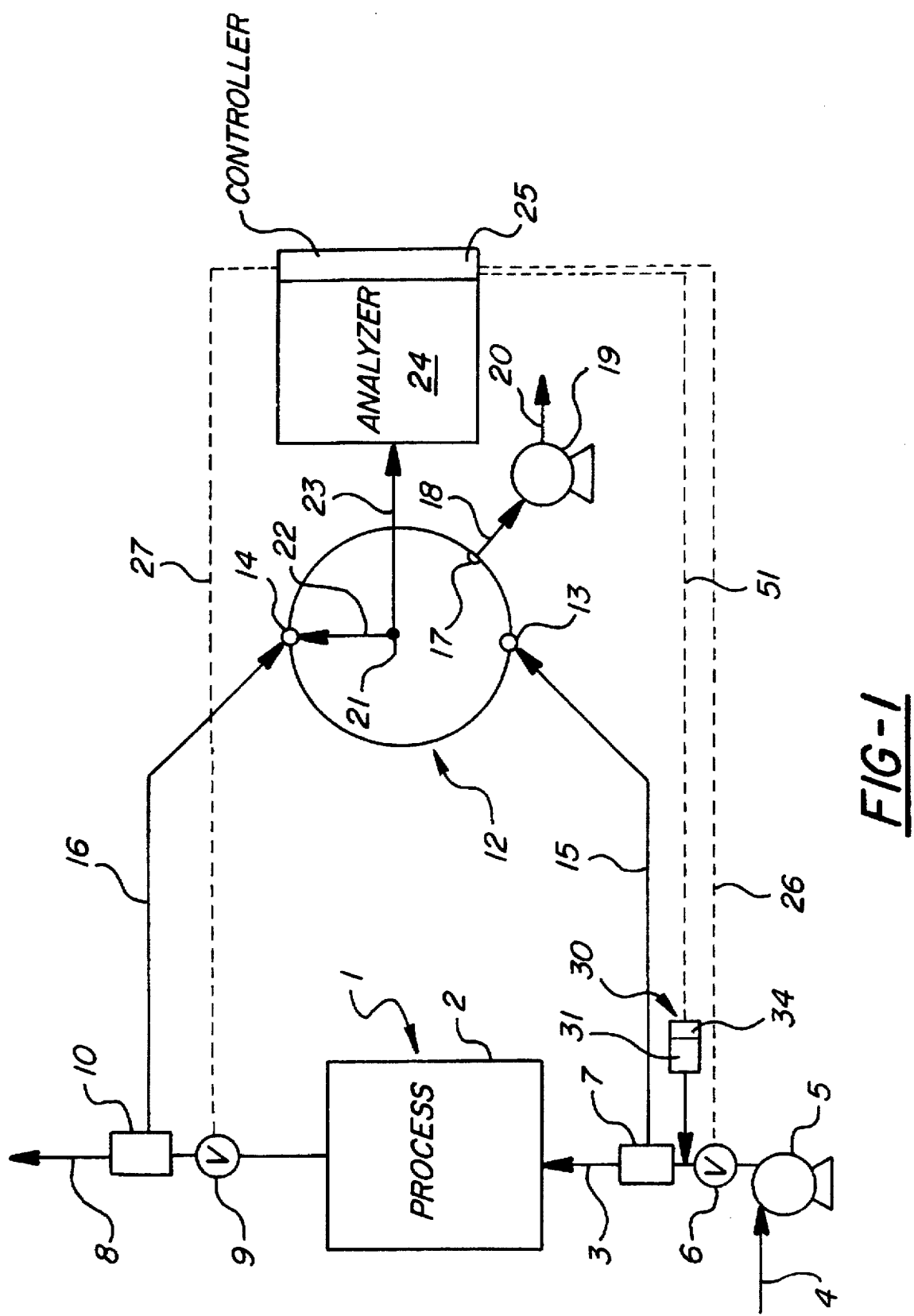
FIG. 1 is a diagrammatic view of a presently preferred embodiment of the invention.

The invention is especially adapted for use in conjunction with the apparatus shown in FIG. 1 which enables organic or other compounds contained in continuously flowing streams of gases or liquids, or both, to be identified and characterized. The apparatus corresponds to that disclosed in the aforementioned patent, to which reference may be had for a more detailed disclosure. Briefly, however, the apparatus comprises a process or treatment zone 1 formed by suitable means such as a retort or reactor 2, into, through, and beyond which a process stream flows. The stream flows toward the reactor through an influent inlet 3 in communication with a gas or liquid source 4 via a variable speed pump 5 and in communication with the reactor 2 via an adjustable, flow control valve 6 and a membrane separator 7.

The process stream may flow into, through, and out of the treatment zone 1 at variable, controlled flow rates as determined by the pump 5, the valve 6, or both. The reactor 2 may be any one of a number of suitable kinds and is capable of containing a solid reagent, such as activated charcoal, an active or inactive biodegrading mass (biomass), or a liquid or a gas in addition to or to the exclusion of the other reagents referred to above. The contents of the reactor will depend upon the specific process streams to which the apparatus is applied, and such process streams include waste water; fermentation reactions; stripping, distillation, and absorption columns; and degasing units, for example.

An effluent outlet 8 communicates with the reactor 2 via an adjustable valve 9 and a membrane separator 10 similar to the separator 7. The outlet 8 communicates also with a drain, vent, the source 4, or other destination as may be appropriate.

The apparatus includes a rotary selector switch 12 having a plurality of inlet ports 13 and 14 connected by tubes 15 and 16 to the membrane separators 7 and 10, respectively. The selector switch has an exhaust port 17 connected via a line 18, an exhaust pump 19, and a tube 20 to a collector, vent, or other suitable device.

The switch 12 has a rotor 21 which carries a coupling tube 22 that may be connected to any selected one of the ports in response to rotation of the rotor. The switch also includes a stationary delivery tube 23 in communication with an analyzer 24. The analyzer is one that is appropriate for analysis of the kinds of analytes extracted from the fluid streams by the separators.

Operatively coupled to the analyzer 24 in known manner is a controller 25. The controller may be a computer such as that designated PDP 11-73 by Digital Equipment Corporation. The controller is connected to a power source (not shown) and to the valves 6 and 9 by control lines 26 and 27, respectively, for adjusting the valves to vary the rates of flow of fluid therethrough.

The membrane of the separator 7 is permeable to a selected compound of interest contained in the influent fluid and the membrane in the separator 10 is permeable to the same or different compound, depending on the treatment occurring in the zone 1, whether the process is one which extracts or adds compounds, and the analysis to be made.

In the use of the apparatus thus far described, influent process liquid is delivered to the treatment zone 1 via the pump 5, the inlet 3, the valve 6, and the membrane separator 7. The rate of flow of the influent liquid is controlled by the pump, the valve, or both. The separator 7 extracts a sample of the selected compound from the influent whence it is delivered to the port 13 of the switch 12 via the tube 15. Movement of the rotor 21 of the switch 12 will establish communication between the port 13 and the analyzer 24 to enable the extract to be identified and characterized.

The liquid delivered to the treatment zone 1 is acted upon by whatever reagent or reagents are accommodated in the reactor 2. The specific reagent utilized will be selected for its ability to react in a known manner with the particular influent fluid and organic or other compounds therein.

Liquid which traverses the reactor 2 will react with the reagent(s) and be discharged through the effluent outlet 8 via the valve 9 and pass through the separator 10 to a collector, drain, or other destination. If the membrane of the separator 10 is permeable to the same compound extracted by the separator 7, it will extract a sample containing some or all of the same compound remaining (if any) in the effluent fluid and deliver it via the tube 16 to the port 14. Adjustment of the rotor 21 to connect the tube 22 to the port 14 will enable the extracted sample to be delivered to the analyzer 24 for analysis.

Whenever the separators 7 and 10 are not being used for analysis purposes, they, their respective tubes 15 and 16, and the ports 13 and 14 are purged by the pump 19, the line 18, and the port 17, it being understood that internal passages are provided in the switch 12 for this purpose, as is conventional.

By comparing the analyses of the influent and effluent fluids, the presence and concentration of the compound of interest in the effluent may be detected and compared with the concentration of such compound in the influent fluid, thereby enabling the effectiveness of the treatment performed in the treatment zone 1 to be evaluated. If it is determined that more or less residence time of the influent fluid in the reactor is required, the valves 6 and 9 may be adjusted appropriately, either manually or automatically by the controller 25 via the connections 26 and 27, respectively.

It also is possible from the comparison of the analyses of the influent and effluent fluid samples to ascertain the effectiveness of the reagent or reagents accommodated in the reactor, thereby enabling appropriate decisions to be made concerning modification or replacement of such reagents.

It will be apparent from the foregoing that the apparatus disclosed thus far is capable of substantially simultaneous on-line analysis of influent and effluent streams, any delay between successive analyses being that necessitated by adjustment of the rotor 21 of the selector switch 12. It also will be apparent that the treatment to which the influent fluid is subjected in the treatment zone may be controlled or varied by adjustment of the rates of flow of such streams. During a given analysis period, however, the rates of flow of the streams should be maintained constant.

The apparatus disclosed herein is intended primarily to evaluate the effectiveness of the treatment performed in the treatment zone 1 with respect to specific organic or other compounds, thereby making it possible to adjust the rate of flow of the streams and/or incorporate in the reactor reagents especially adapted for use with such compounds. This objective may be achieved by injecting into the influent stream a known quantity of a known organic or other compound, dissolving the compound in the stream, and analyzing both the influent and effluent streams as described. Injection of the known compound may be achieved by spiking apparatus 30 that is best shown in FIGS. 2 and 3.

The spiking apparatus 30 includes a source 31 of a selected compound. For illustrative purposes the source is shown as constituting a syringe pump corresponding to that manufactured by Sage Instruments and having a barrel 32 within which is a plunger 33 driven incrementally or continuously at a selected speed by a variable speed motor 34, depending on whether the treatment is a batch or a continuous process. The plunger has adjacent its inner end a groove in which is accommodated a sealing O-ring 35. At the discharge end of the barrel is a fitting 36 to which is connected one end of a tube 37, the opposite end of which is accommodated in a fitting 38 from which a hollow needle 39 extends. Suitable seals 40 encircle one end of the needle 39 whereas the opposite end thereof extends into a cavity 41 formed in one branch 42 of a Tee fitting 43 which communicates with the interior of the influent conduit 3 between the valve 6 and the separator 7. The cavity 41 is closed by a seal 44.

Accommodated within the needle 39 is a capillary tube 45 having a bore of greatly reduced diameter compared to the diameters of the bores of the needle and the tube 37. For example, the bore of the tube 45 may be such as to provide a calculated 400-fold increase in linear velocity of the fluid substance dispensed from the syringe barrel 32. This construction is one that is especially adapted for injecting organic or other substances into the conduit 3 that are nominally immiscible with the influent fluid. The velocity at which such substances are injected into the contents of the influent conduit 3 results in adequate dissolution of the spiking substance in the influent liquid.

An appropriate material for the tube 45 is fused silica or any other material that is inert to the injected compound. The free end of the tube 45 constitutes a nozzle for injecting the selected substance directly into the influent liquid in the cavity 41. In some instances it may be desirable to disperse the spiking compound in a substance, such as acetone, that is miscible in both the spiking compound and the influent to facilitate dissolution of such compound in the process stream.

It is preferred to interpose a mixing vessel 46 between the spiking apparatus 30 and the membrane separator 7 to ensure thorough mixing of the influent and to provide a trap for any particulate material which may be entrained in the stream. Such a vessel includes a cap 47 through which inlet and outlet tubes 48 and 49, respectively, pass in sealed relation. Within the vessel is a magnetic stirrer 50 or other suitable agitator.

In the use of the apparatus a known quantity of the known spiking compound is injected into and dissolved in the process stream influent and delivered to the treatment zone 1 via the inlet 3 and the separator 7. The solution delivered to the treatment zone 1 is subjected to treatment by the reagents in the reactor 2, following which the treated influent is discharged from the reactor via the conduit 8, the valve 9, and the separator 10. The compounds separated in the separators 7 and 10 are delivered to the switching valve 12 for analysis independently of one another by the analyzer 24.

The rotary switching valve 12 and the analyzer 24 make it possible to compare on-line at any selected time the concentration of a selected compound in the spiked influent and the concentration of such compound in the treated effluent. The effectiveness of the treatment of the influent fluid performed in the treatment zone 1 may be ascertained by comparing the results of the analyses of the influent and effluent streams.

The injection of the spiking fluid is accomplished by movement of the plunger 33 of the pump 31 in a direction to dispense the contents of the barrel 32. This may be accomplished manually, but it is preferred to activate the spiking apparatus automatically in accordance with a predetermined program. Thus, the controller 25 may be coupled by a power line 51 to the motor 34 forming part of the syringe pump to advance the plunger continuously or at predetermined intervals and inject a known quantity of a selected compound into the influent fluid. Alternatively, any controllable speed pump may be used to deliver the spiking compound to the stream. The selected compound is one that is extractable in the separators 7 and 10.

The ability to inject and dissolve a known quantity of a known organic or other compound in a chemical process stream upstream from a treatment zone make it possible to determine not only what kind of treatment should be performed on such stream to remove such compound, but also the efficiency of such treatment.

We claim:

1. Apparatus for on-line analysis of a fluid stream flowing to, through, and from a treatment zone, said apparatus comprising means for delivering said stream to said zone; means for dispensing and dispersing into said stream upstream from said zone a known compound from a supply thereof, said compound including a substance that is at least partially immiscible with said stream; reagent means in said zone for treating said stream to remove said compound from said stream; means for sampling said stream downstream from said zone to separate therefrom an extract containing at least a portion of any of said compound remaining in said stream following treatment in said zone; means for analyzing the extract to detect the presence of said compound therein; and means for delivering the extract to said analyzing means.

2. Apparatus according to claim 1 wherein said dispensing and dispersing means accelerates said compound to a velocity sufficient to partially dissolve said substance in said fluid stream.

3. Apparatus according to claim 2 wherein said dispensing and dispersing means accelerates said compound to a velocity up to about 400 times the rate at which said compound is dispensed from said supply.

4. Apparatus according to claim 2 wherein said dispensing and dispersing means comprises a conduit having a bore of predetermined diameter in communication with said supply, and a tube accommodated in said bore, said tube having a bore through which said compound must pass and whose diameter is less than that of the bore of said conduit.

5. Apparatus according to claim 4 wherein said supply comprises a hollow barrel in communication with said conduit and a displaceable plunger in said barrel for dispensing said compound from said barrel into said conduit.

6. Apparatus according to claim 5 including means for displacing said plunger at a selected velocity.

* * * * *